United States Patent [19]
Kirschner et al.

[11] Patent Number: 5,955,288
[45] Date of Patent: Sep. 21, 1999

[54] RECEPTOR-TYROSINE KINASE ASSAY IN YEAST

[75] Inventors: Marc W. Kirschner, Newton; Noriyuki Kinoshita, Boston, both of Mass.

[73] Assignee: President and Fellows of Harvard College, Cambridge, Mass.

[21] Appl. No.: 08/733,489

[22] Filed: Oct. 18, 1996

Related U.S. Application Data

[62] Division of application No. 08/279,217, Jul. 22, 1994, Pat. No. 5,573,944.
[51] Int. Cl.$^6$ ........................................ C12N 15/81
[52] U.S. Cl. ............................. 435/7.2; 45/7.1; 45/172.3
[58] Field of Search ........................... 435/7.1, 7.2, 172.3

[56] References Cited

PUBLICATIONS

King et al., "Control of Yeast Mating Signal Transduction by a Mammalian beta2–Adrenergic Receptor and GS alpha subunit", Science 250:121–123, Oct. 5, 1990.

Miki et al. "Expression cDNA Cloning of the KGF Receptor by Creation of a Transforming Autocrine Loop", Science 251:72–75, Jan. 4, 1991.

Florio et al., *Molecular Biology of the Cell* 5: 283 (1994).

Keating and Williams, *Science* 239: 914 (1988).

*Primary Examiner*—John Ulm
*Attorney, Agent, or Firm*—Kevin M. Farrell

[57] ABSTRACT

Disclosed herein are compositions and methods which are useful in the identification and isolation of components involved in transmembrane receptor-mediated signaling. Such components include the receptors themselves (e.g., tyrosine kinase receptors, cytokine receptors and tyrosine phosphatase receptors), as well as ligands which bind the receptors and modulators of the downstream intracellular catalytic event which characterizes receptor-mediated signalling.

14 Claims, 3 Drawing Sheets

RECEPTOR-TYROSINE KINASE ASSAY IN YEAST

This application is a division of application Ser. No. 08/279,217, filed Jul. 22, 1994 now U.S. Pat. No. 5,573,944.

GOVERNMENT SUPPORT

Experimental work described herein was supported by grants from the United States Government which may have certain rights in the invention.

BACKGROUND OF THE INVENTION

Transmembrane receptors are proteins which are localized in the plasma membrane of eukaryotic cells. These receptors have an extracellular domain, a transmembrane domain and an intracellular domain. Transmembrane receptors mediate molecular signaling functions by, for example, binding specifically with an external signaling molecule (referred to as a ligand) which activates the receptor. Activation results typically in the triggering of an intracellular catalytic function which is carried out by, or mediated through, the intracellular domain of the transmembrane receptor.

There are various families of transmembrane receptors that show overall similarity in sequence. The highest conservation of sequence is in the intracellular catalytic domain. Characteristic amino acid position can be used to define classes of receptors or to distinguish related family members. Sequences are much more divergent in the extracellular domain.

A variety of methods have been developed for the identification and isolation of transmembrane receptors. This is frequently a straightforward matter since receptors often share a common sequence in their catalytic domain. However, the identification of the ligands which bind to, and activate, the transmembrane receptors is a much more difficult undertaking. Brute force approaches for the identification of ligands for known receptors are rarely successful. Brute force approaches usually depend on a biological activity that approaches usually depend on a biological activity that can be monitored (e.g., nerve growth for nerve growth factor; or glucose homeostasis for the insulin receptor) or they depend on finding a source of the ligand and using affinity to purify it (as was used to find the c-Kit ligand in mouse hemopoietic cells). In general, however, a source of the ligand is not known, nor is there an obvious or easily assayable biological activity. Therefore, there are many receptors, referred to as "orphan receptors", for which no corresponding ligand has been identified. A systematic approach to the identification of receptor ligands would be of great value for the identification of ligands having useful pharmacological activities.

SUMMARY OF THE INVENTION

The present invention relates to compositions and methods which are useful in connection with the identification of transmembrane receptors and their corresponding ligands. Preferred transmembrane receptors include tyrosine kinase receptors, cytokine receptors and tyrosine phosphatase receptors. Such receptors mediate cell signaling through the interaction of specific binding pairs (e.g., receptor/ligand pairs). The present invention is based on the finding that an unknown component in a receptor-mediated signaling pathway, which results ultimately in an intracellular catalytic event, can be identified by combining other known components within a cellular background within which the catalytic event ordinarily will not take place at significant levels. A cDNA expression library is then used to transform such cells. If the cDNA insert encodes the missing component of the transmembrane receptor-mediated signaling pathway, the catalytic event will be triggered. Detection of the otherwise absent catalytic activity is indicative of a cDNA insert encoding the missing component.

DETAILED DESCRIPTION OF THE INVENTION

Figure 1A:
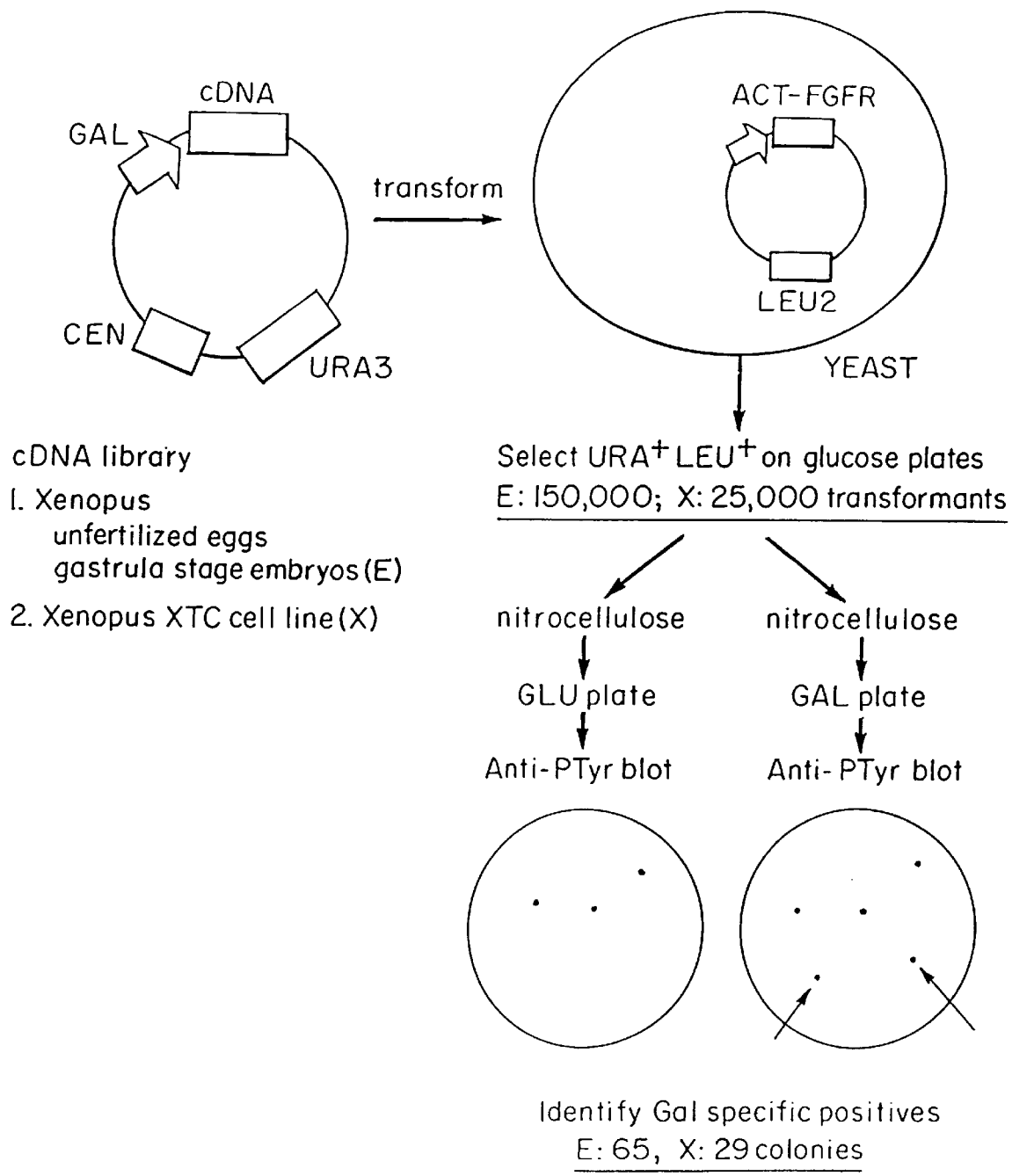
FIG. 1 is a diagram illustrating the steps employed in the identification of a ligand specific for the FGF receptor.

Transmembrane receptors have a binding site with high affinity for a specific signaling molecule. The signaling molecule is referred to herein as a ligand. The present invention is based on the development of a novel approach for the identification of polypeptide ligands by functional expression in the yeast *Saccharomyces cerevisiae*. This approach is based on the previously unproven hypothesis that it may be possible to functionally express a heterologous tyrosine kinase receptor and its corresponding polypeptide ligand in the same yeast cell, leading to the activation of the receptor and a substantial increase in intracellular tyrosine phosphorylation. The intracellular tyrosine kinase activity of the tyrosine kinase receptor is activated by the binding of a ligand to the extracellular domain of the receptor. This interaction can occur on the surface of the cell (plasma membrane) or in intracellular membrane compartments such as secretory vesicles. In either case, according to the hypothesis confirmed herein, the activation of the cytoplasmically oriented kinase domain results in phosphorylation of tyrosine residues of cytoplasmic protein targets.

Yeast was chosen as an expression system because many molecular biological techniques are available and it has been demonstrated that many higher eukaryotic genes, including some growth factor-encoding genes, can be functionally expressed in yeast. In addition, only a few endogenous protein tyrosine kinases have been identified in yeast, so that yeast is expected to have a low background of endogenous tyrosine phosphorylation. These features enabled the development of a screen to identify polypeptide ligands for heterologous tyrosine kinase receptors for which no ligand has yet been identified. Such receptors are referred to as orphan receptors. The term heterologous is used herein to mean "non-endogenous". Thus, for example, a tyrosine kinase which is heterologous in the yeast *Saccharomyces cerevisiae* is a tyrosine kinase which is non-endogenous (i.e., not present) in wild-type *Saccharomyces cerevisiae*.

The disclosed method for identifying a ligand for a tyrosine kinase receptor involves the co-expression in yeast cells (preferably *Saccharomyces cerevisiae*) of a gene encoding a tyrosine kinase receptor, together with an expression cDNA library which, for example, is constructed from a tissue or cell line that is thought to synthesize a receptor ligand in vivo. The tyrosine kinase gene, together with any regulatory elements required for expression, can be introduced into the yeast strain on a stable plasmid (e.g., a CEN-based plasmid), or it can be integrated into the yeast chromosome using standard techniques (*Methods In Enzymology*, vol. 194, C. Guthrie and G. Fink, eds., (1991)).

The choice of expression vectors for use in connection with the cDNA library is not limited to a particular vector.

Any expression vector suitable for use in yeast cells is appropriate. The discussion relating to experiments disclosed in the Exemplification section which follows describes a particular combination of elements which was determined to yield meaningful results. However, many options are available for genetic markers, promoters and ancillary expression sequences. As discussed in greater detail below, the use of an inducible promoter to drive expression of the cDNA library is a preferred feature which provides a convenient means for demonstrating that observed changes in tyrosine kinase activity are, in fact, cDNA dependent.

In a preferred format of the assay, two expression constructs are employed; the first expression construct contains the tyrosine kinase gene and the second expression construct carries the cDNA library. Typically the two expression constructs are not introduced simultaneously, but rather a stable yeast strain is first established which harbors the tyrosine kinase receptor carried on a CEN-based plasmid. Other regulatory sequences are included, as needed, to ensure that the tyrosine kinase gene is constitutively expressed. A CEN-based expression vector contains CEN sequences which are specific centromeric regions which promote equal segregation during cell division. The inclusion of such sequences in the expression construct results in improved mitotic segregation. It has been reported, for example, that mitotic segregation of CEN-based plasmids results in a population of cells in which over 90% of the cells carry one to two copies of the CEN-based plasmid. Faulty mitotic segregation in a similar transformation experiment with an otherwise identical expression construct which lacks CEN sequences would be expected to result in a cell population in which only about 5–20% of the cells contain the plasmid.

Many transmembrane tyrosine kinase receptors have been identified (for reviews see, e.g., Hanks, *Current Opinion in Structural Biology* 1: 369 (1991) and Pawson and Bernstein, *Trends in Genetics* 6: 350 (1990)). A number of these tyrosine kinase receptors are orphan receptors for which no activating ligand has been identified. Any transmembrane tyrosine kinase that can be expressed in yeast cells is useful in connection with the present invention. Based on fundamental principles of molecular biology, there is no reason to believe a priori that any member of the tyrosine kinase receptor family would not be useful in connection with the present invention. Preferably, the gene encoding the tyrosine kinase receptor is isolated from the same organism from which nucleic acid is to be isolated for use in the construction of a cDNA library.

As discussed in the Exemplification section which follows, the level of expression of the transmembrane tyrosine kinase is a variable which must be considered in the design of the assay for ligand identification. For example, it was determined that high level expression of the FGF receptor results in a substantial increase in intracellular phosphorylation, even in the absence of FGF. Therefore, it is important that expression of the transmembrane receptor be driven by regulatory elements which result in a sufficient level of expression of the transmembrane receptor to facilitate detection following activation of the receptor by ligand binding, while not resulting in overexpression to the extent that ligand-independent autophosphorylation results. A preferred promoter for the expression of the transmembrane receptor is the ACT1 (actin) promoter. This promoter was determined to provide a robust, ligand-dependent signal in the experiments described below.

The cDNA library is prepared by conventional techniques. Briefly, mRNA is isolated from an organism of interest. An RNA-directed DNA polymerase is employed for first strand synthesis using the mRNA as template. Second strand synthesis is carried out using a DNA-directed DNA polymerase which results in the cDNA product. Following conventional processing to facilitate cloning of the cDNA, the cDNA is inserted into an expression vector suitable for use in yeast cells. Preferably the promoter which drives expression from the cDNA expression construct is an inducible promoter (e.g., GAL1).

As disclosed in the Exemplification section that follows, removal of the endogenous signal sequence from a cDNA insert encoding a functional receptor ligand resulted in inactivation of the ligand. It appears, therefore, to be necessary to include a signal sequence in the cDNA library constructs to mark the encoded polypeptide for transport across the membrane of the endoplasmic reticulum thereby enabling the extracellular release of the encoded polypeptide which facilitates interaction with the extracellular domain of a transmembrane receptor. The signal sequence employed in the experiments disclosed herein was the signal sequence of *Saccharomyces cerevisiae* invertase. However, any signal sequence which can function in yeast should be useful in connection with the present invention (Nothwehr and Gordon, *Bioessays* 12: 479 (1990)).

The cDNA expression library is then used to transform the yeast strain which constitutively expresses the transmembrane tyrosine kinase gene. mRNA encoding the tyrosine kinase receptor and the cDNA product are thought to be translated in the rough endoplasmic reticulum, accumulate in the inner cavity of the rough endoplasmic reticulum, and migrate to the lumen of the Golgi vesicles for transport to the Golgi complex. Within the Golgi complex, proteins are "addressed" for their ultimate destination. From the Golgi complex, the addressed proteins are transported out of the complex by secretory vesicles.

A transmembrane tyrosine kinase receptor, if sequestered in a secretory vesicle, the Golgi complex or the endoplasmic reticulum, is oriented such that the cytoplasmic domain is in contact with the cellular cytoplasm as the various vesicles migrate from the Golgi complex to the plasma membrane which is the ultimate destination for a transmembrane receptor. It is possible that the signal sequence bearing polypeptides encoded by the cDNA library can be co-compartmentalized with the transmembrane receptor in the same secretory vesicle. If this were to occur, any cDNA encoded ligand specific for the tyrosine kinase receptor could bind with the "extracellular" portion of the tyrosine kinase receptor (which is located in the internal portion of the secretory vesicle during the migration to the plasma membrane) thereby activating intracellar tyrosine kinases through contact with the cytoplasmically oriented intracellular domain of the tyrosine kinase receptor.

Alternatively, activation of intracellular tyrosine kinase activity could also result from interaction with an extracellular polypeptide encoded by the cDNA library through interaction with a plasma transmembrane tyrosine kinase receptor. This occurs, for example, following migration of the secretory vesicle to the plasma membrane resulting in the incorporation of the plasma transmembrane tyrosine kinase receptor and export of the signal sequence-bearing cDNA encoded polypeptide ligand.

In either case, activation of the intracellular tyrosine kinase activity results in the phosphorylation of intracellular tyrosine residues at a level which is substantially higher (i.e., at least about 4-fold higher) than background levels of phosphorylation in the yeast stain harboring an expression construct containing only the gene encoding the tyrosine kinase receptor (the negative control strain).

Figure 2:
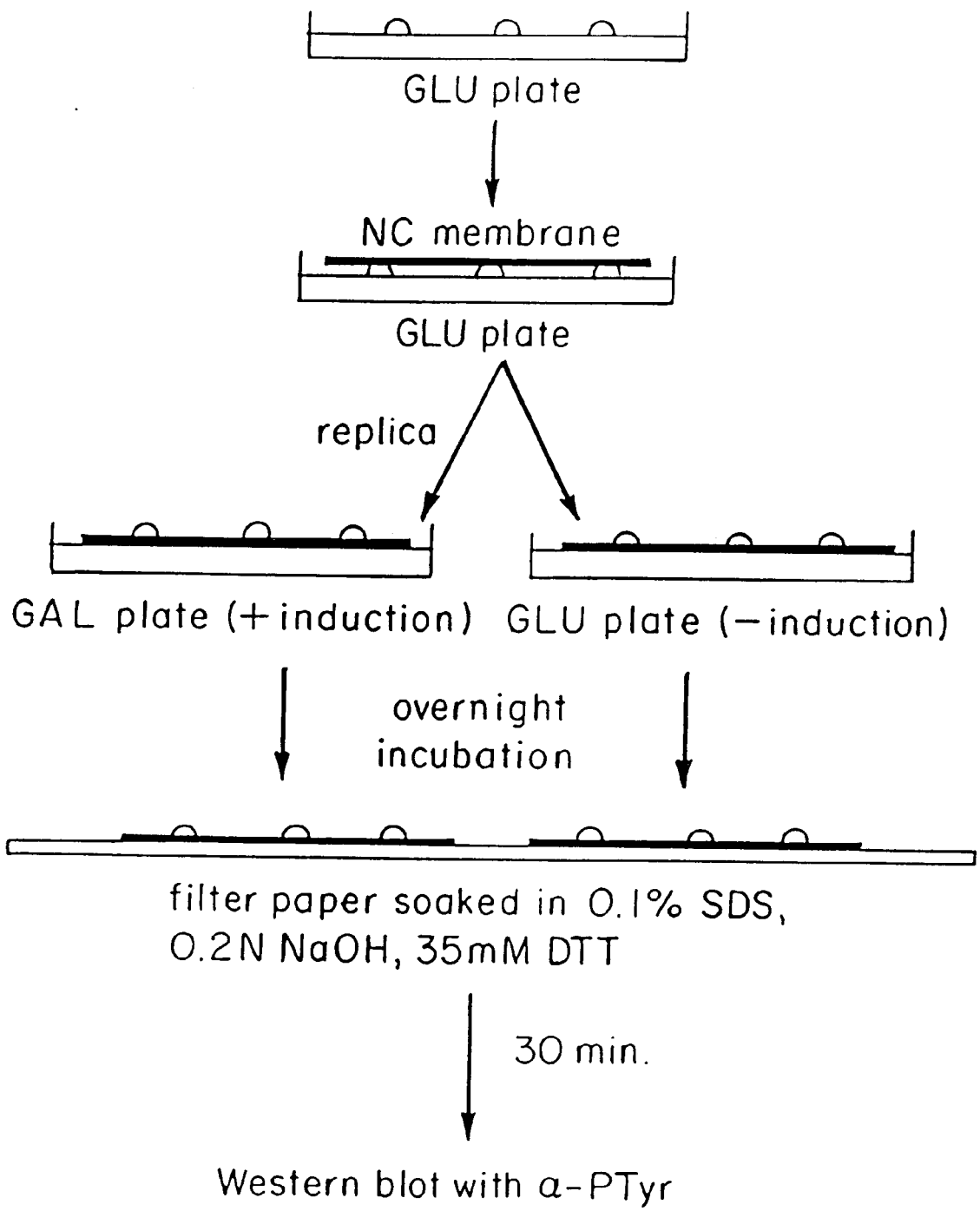
FIG. 2 is a diagram illustrating the colony Western blot technique.

The preferred method for determining the level of intracellular tyrosine phosphorylation is a colony Western blot using replica plates. It will be recognized that, although particularly convenient, the colony Western blot method is but one example of many conventional assays which could be employed to determine levels of intracellular tyrosine kinase activity. The colony Western blot procedure using replica plates is shown diagramatically in FIG. 2. cDNA library transformants are initially plated on media which do not contain an inducer of the promoter which drives expression of the cDNA insert. For examples, if the GAL1 promoter is used to drive expression of the cDNA insert, cDNA library transformants are initially plated on a medium containing 2% glucose. On this growth medium, cells containing the cDNA expression construct will grow, but the encoded cDNA product is not expressed.

A set of replica filters is produced from the initial transformation plate by sequentially placing a set of directionally oriented membranes (e.g., nitrocellulose filter membranes) over the transformation plate such that the membrane contacts existing transformant colonies. Cells from transformation colonies adhere to the membranes to form a pattern which represents the pattern of colonies on the transformation plate. Each of the replica filters is then placed on a separate plate, one of which contains a compound which will induce the inducible promoter (e.g., 2% galactose to induce the GAL1 promoter) and one of which will not induce the inducible promoter (e.g., 2% glucose for the GAL1 promoter). Both plates are incubated overnight to promote regrowth of the original cDNA library transformants.

Following overnight incubation, the replica filters are removed from the growth medium plates, and the colonies are lysed in situ by soaking the replica filters in a lysis solution for a period of time sufficient to lyse cellular membranes (e.g., 0.1% SDS, 0.2 N NaOH, 35 mM DTT for about 30 minutes). The replica filters are then probed with anti-phosphotyrosine antibodies. Colonies which exhibit elevated tyrosine kinase activity on the replica filter which had been incubated overnight on a growth medium containing a compound which induces expression of the cDNA insert linked to the inducible promoter, but which do not exhibit elevated tyrosine kinase activity on the replica filter incubated overnight on a growth medium lacking the inducing compound, contain a cDNA insert encoding a candidate ligand.

To confirm that a candidate ligand is, in fact, a ligand (and not, for example, a distinct tyrosine kinase), the expression construct is recovered (or rescued) from the cells of the colony demonstrating increased tyrosine kinase activity when grown under inducing conditions. The rescued expression construct is then used to transform a first yeast strain which is known to constitutively express the tyrosine kinase gene, and a second yeast strain which does not express the tyrosine kinase gene. Increased tyrosine kinase activity in the strain which is known to express the tyrosine kinase gene, coupled with no increased tyrosine kinase activity in the strain which does not express the tyrosine kinase gene, serves as confirmation that the cDNA insert of the cDNA expression construct encodes a polypeptide ligand which binds to, and activates, the tyrosine kinase gene product.

Following confirmation that the candidate ligand is, in fact, a receptor ligand, it is a straightforward matter to identify and characterize the polypeptide encoded by the cDNA library which is responsible for the increase in tyrosine kinase activity. This is accomplished by isolating plasmid DNA from the strain which exhibits the elevated tyrosine kinase activity and characterizing the insert carried in the plasmid (e.g., by DNA sequence analysis). The molecule encoded by the cDNA insert can then be further characterized by conventional approaches such as expression and isolation of the encoded polypeptide followed by in vitro binding studies in order to confirm the specificity of the binding interaction with the transmembrane receptor.

The method of the present invention is not limited to the isolation of tyrosine kinase receptor ligands. Rather, the method can be modified for use in the identification of ligands for any transmembrane receptor having a single transmembrane domain, an extracellular domain and an intracellular domain. This is accomplished by generating an expression construct encoding a chimeric fusion protein comprising the extracellular domain of a transmembrane receptor fused to the intracellular domain of a specific tyrosine kinase receptor (e.g., the FGF receptor). As mentioned previously, this construct is preferably generated in a CEN-based plasmid background or, alternatively, in a plasmid which will facilitate integration of the chimeric receptor into the yeast chromosome. Conventional molecular biological techniques are employed to generate this construct, as well as all others disclosed in this specification (see e.g., *Molecular Cloning: A Laboratory Manual*, Maniatis et al., eds., Cold Spring Harbor Publications, Cold Spring Harbor, N.Y. (1989)). This expression construct encoding the tyrosine kinase receptor fusion protein is used in a manner analogous to the expression construct encoding the tyrosine kinase receptor in the embodiment described above.

Briefly, the preferred embodiment of this aspect of the invention includes the construction of a yeast strain which constitutively expresses a chimeric fusion protein of the type described above. This strain is then transformed with a cDNA expression library generated using mRNA isolated from the organism of interest. A ligand which binds specifically to the native transmembrane receptor will bind to the extracellular domain of the tyrosine kinase fusion protein and this ligand binding will trigger ligand-dependent intracellular tyrosine kinase activity mediated by the intracellular domain of the tyrosine kinase receptor. Intracellular tyrosine kinase activity is detected in the manner described previously.

A specific example of this embodiment of the present invention is applicable to the isolation of a ligand for a cytokine receptor (e.g., erythropoietin receptor, interleukin-3 receptor, etc.). Cytokine receptors, like tyrosine kinase receptors, are transmembrane receptors found in mammalian cells and possess both an extracellular domain and an intracellular domain. However, unlike the tyrosine kinase receptors, cytokine receptors do not possess a catalytic domain but rather recruit cytoplasmic tyrosine kinase enzymes in response to ligand activation. More specifically, the intracellular (cytoplasmic) domain of the cytokine receptor has been shown to bind to, and activate, a class of cytoplasmic tyrosine kinases (e.g., the JAK2/TYK2 class).

To isolate cytokine receptor ligands, a yeast strain is constructed which constitutively expresses a cytoplasmic tyrosine kinase and a transmembrane cytokine receptor. This yeast strain is then transformed with a cDNA expression library from an organism of interest, preferably under the control of an inducible promoter. Elevated levels of tyrosine kinase activity will be observed if the polypeptide encoded by the cDNA library insert functions as a ligand for the native cytokine receptor. Binding of the polypeptide ligand to the extracellular domain of the cytokine receptor (either at the plasma membrane or within a secretory vesicle) results in the activation of the cytoplasmic tyrosine kinase.

The colony Western blot procedure discussed above, and shown diagramatically in FIG. 2, is the preferred method for screening for an expression construct encoding a functional ligand. Specifically, a set of replica filters is prepared from the original transformation plate and the first and second replica filters are incubated overnight under inducing conditions, and non-inducing conditions, respectively. Colonies affixed to the replica filters are then lysed and probed with anti-phosphotyrosine antibodies.

Increased levels of tyrosine kinase activity can be indicative of a cDNA insert encoding a ligand for the cytokine receptor or, alternatively, a cDNA insert encoding a cytoplasmic tyrosine kinase enzyme. To determine which of these two alternatives is responsible for the observed increase in tyrosine kinase activity, the expression construct encoding the candidate ligand is rescued and used to independently transform a first cell population which constitutively expresses the cytokine receptor and the cytoplasmic tyrosine kinase, and a second cell population which constitutively expresses the cytokine receptor but not the cytoplasmic tyrosine kinase. Candidates which demonstrate an increase in tyrosine kinase activity in the first cell population, but not the second, encode a cytokine receptor ligand. Expression constructs which result in an increase in tyrosine kinase activity in both the first cell population and the second cell population encode a cytoplasmic tyrosine kinase.

Given the fundamental disclosure that a yeast cell system can be used to identify ligands and other members of specific binding pairs involved in receptor-mediated molecular signaling, numerous variations of the theme described above are derivable through routine experimentation. Using such variations, any single polypeptide component of the receptor-mediated signaling pathway can be identified through the introduction of a cDNA library into yeast cells which have been modified to constitutively produce other necessary components of the signaling pathway.

For example, the methods described above can be modified to facilitate the identification of a cytokine receptor. As discussed above, cytokine-receptor mediated signaling involves a cytokine receptor and a cytoplasmic tyrosine kinase which is activated by interaction with the cytoplasmic domain of the cytokine receptor. As reported in the Exemplification section below, overexpression of the transmembrane tyrosine kinase (e.g., by expression from the GAL1 promoter) resulted in ligand-independent tyrosine kinase activity. By analogy, it would be expected that overexpression of a transmembrane cytokine receptor in the presence of a cytoplasmic tyrosine kinase would yield ligand-independent tyrosine kinase activity.

More specifically, a yeast strain constitutively expressing a cytoplasmic tyrosine kinase is first constructed. The use of the GAL1 promoter would be expected to result in a high level of cytoplasmic tyrosine kinase expression. However, routine experimentation may be required to optimize the expression level. It is preferred, for example, that the cytoplasmic tyrosine kinase be produced at such a level that it is detectable by Western blot.

A cDNA library is then constructed, preferably with the expression of the cDNA insert under the control of an inducible promoter. Replica filters are produced and incubated independently with, and without, a compound capable of inducing expression from the inducible promoter. Increased levels of tyrosine kinase activity are detected, for example, by colony Western blot in cells grown under inducing conditions, but not under non-inducing conditions. This would be observed, for example, when the cDNA insert encodes a cytokine receptor. The expression construct is rescued from these cells and introduced independently into yeast cells with, and without, constitutively expressed intracellular tyrosine kinase. Increased tyrosine kinase activity which is dependent upon the constitutively expressed cytoplasmic tyrosine kinase of the host strain indicates that the cDNA insert encodes a cytokine receptor. Increased tyrosine kinase activity which is not dependent upon the constitutively expressed cytoplasmic tyrosine kinase of the host strain is an indication that the cDNA insert encodes a functional tyrosine kinase. If such a cytokine receptor is known or discovered, yeast strains expressing the cytoplasmic tyrosine kinase and the cytbkine receptor can be employed in a method for the isolation of a ligand in a manner analogous to the methods described elsewhere in this specification.

Another example of a variation of presently disclosed method is useful for the identification of a receptor for an orphan polypeptide ligand (i.e., a ligand for which no receptor has been previously identified), or for the identification of new receptors for a ligand which is known to interact productively with one or more previously identified receptors. This method incorporates the use of a yeast strain which has been modified to constitutively produce the previously identified ligand or orphan ligand. A cDNA library is introduced and the colony Western blot is employed to identify colonies which exhibit increased tyrosine kinase activity in the induced state. Rescue of the expression construct, followed by retransformation of yeast cells both with and without a constitutively expressed ligand, is used to confirm ligand-dependent activation of tyrosine kinase activity. It will be recognized that the description above relates specifically to a tyrosine kinase-like receptor. The method is easily modified for use with a cytokine receptor by adding constitutive cytoplasmic tyrosine kinase activity to the list of constitutive host cell requirements.

Similarly, the methods of this invention can be used to identify a cytoplasmic tyrosine kinase if a known cytokine receptor and ligand are provided. In this method, the cytokine receptor and ligand are expressed constitutively in a host yeast strain. The cDNA library is provided, and transformants are screened, in the induced and non-induced state, by the replica method discussed above. Candidate cytoplasmic tyrosine kinases are those encoded by an expression construct conferring increased tyrosine kinase activity in the induced state. The cDNA expression construct is rescued from the identified colony and introduced into yeast cells which constitutively express the cytokine receptor and ligand. The rescued construct is also introduced into a yeast strain lacking the cytokine receptor and ligand. Increased activity in the former, but not in the latter, is indicative of a cDNA insert encoding a cytoplasmic tyrosine kinase.

In another aspect of the invention, polypeptide modulators of receptor-mediated tyrosine kinase activity can be isolated. A polypeptide modulator can be, for example, a polypeptide (intracellular or extracellular) which modifies the affinity of the ligand for receptor, or which modifies the activity of the catalytic domain (either integral or recruited). Polypeptide modulators can be isolated by first providing a yeast strain which constitutively expresses a ligand/receptor pair (together with the cytoplasmic tyrosine kinase in the case of a cytokine receptor/ligand pair). The construction of such strains has been discussed in greater detail above. A yeast cell which constitutively expresses the ligand/receptor pair is expected to exhibit a relatively high level of background tyrosine kinase activity when the cDNA library is expressed in both the induced and non-induced state. However, the presence of a cDNA insert encoding a strong modulator (either an up-modulator or a down-modulator) will be determined by a detectable (i.e., at least about 2-fold) change in the level of tyrosine kinase activity in the induced state due to the presence of the polypeptide modulator.

In another aspect of the invention, ligands which specifically activate transmembrane tyrosine phosphatase receptors can be isolated. Transmembrane tyrosine phosphatase receptors are membrane components which have an intracellular catalytic domain which functions to remove phosphate groups from tyrosine residues. In other words, the tyrosine phosphatase receptor function can be viewed as a catalytic function which reverses the action of a tyrosine kinase (a tyrosine kinase functions by adding a phosphate group to intracellular tyrosine residues). Tyrosine phosphatase receptors have an extracellular domain and, therefore, the existence of extracellular ligands is presumed although none have been isolated to date.

In order to isolate a cDNA fragment encoding a tyrosine phosphatase receptor ligand, it is necessary to first provide a yeast strain which constitutively expresses cellular components necessary to produce a basal level of intracellular tyrosine kinase activity. This can be accomplished, for example, by providing a strain which constitutively expresses appropriate levels of a transmembrane tyrosine kinase receptor, together with its corresponding ligand. Basal levels of tyrosine kinase activity in such a strain are determined using the colony Western blot, for example.

Following a determination of intracellular tyrosine kinase activity, this strain is further modified to express a tyrosine phosphatase receptor. Subsequent to the introduction of the tyrosine phosphatase receptor gene, levels of tyrosine kinase activity are again determined to ensure that there has been no change in the basal level of phosphorylation detected. In the absence of the tyrosine phosphatase receptor ligand, the addition of the expressible tyrosine phosphatase receptor gene to the strain should not affect basal levels of phosphorylation.

Confirmation that the introduction of the tyrosine phosphatase gene does not affect detected phosphorylation levels is followed by the introduction of a cDNA library, preferably under the control of an inducible promoter. Replica filters are produced from the plate of transformants and incubated overnight under either inducing or non-inducing conditions. The levels of intracellular tyrosine phosphorylation are then determined, for example, by the colony Western blotting procedure. Reduced levels of intracellular tyrosine phosphorylation under inducing growth conditions, relative to the levels determined under non-inducing growth conditions, are an indication that the cDNA insert encodes a tyrosine phosphatase ligand which binds to the extracellular domain of the tyrosine phosphatase receptor thereby activating the tyrosine phosphatase activity which functions to reduce intracellular tyrosine phosphorylation thereby reversing the effect of the constitutively expressed tyrosine kinase. The initial indication that the cDNA insert encodes a tyrosine phosphatase ligand can be confirmed by further studies including, for example, demonstration that the observed decrease in phosphorylation is dependent upon entry of the cDNA encoded product into the secretory pathway. Confirmation that a signal sequence is encoded by the cDNA insert is an example of one type of confirmatory experiment.

The methods of the present invention can be further modified for use in the identification of functionally significant domains in a transmembrane receptor or its ligand. This method is carried out, for example, by mutagenizing either the transmembrane receptor or its ligand by conventional site-directed mutagenic techniques. The mutagenized component is then included in an assay of the type described above with a non-mutagenized copy serving as a positive control. Increased intracellular tyrosine phosphorylation in the positive control coupled with a relative decrease in tyrosine phosphorylation (relative to the positive control) in the assay which includes the mutagenized component indicates that the mutagenized amino acid residue(s) are of functional significance.

EXEMPLIFICATION

Disclosed in this Exemplification section are experiments which confirm a previously unproven hypothesis that it may be possible to functionally express a tyrosine kinase receptor and its corresponding polypeptide ligand in the same yeast cell, leading to activation of the receptor and a substantial increase in intracellular tyrosine phosphorylation. More specifically, using African clawed frog Xenopus laevis FGF receptor and FGF genes as a model system, it has been demonstrated that tyrosine kinase activity is triggered by co-expression of its ligand gene in yeast cells, provided that the ligand is capable of entering the secretory pathway. This activation of FGF receptor was detected by colony Western blotting which enables the screening of a large number of yeast transformants of a cDNA library. By screening a Xenopus cDNA library with a yeast strain expressing FGF receptor, two genes encoding novel growth factor-like ligands were identified, which can activate the FGF receptor by conventional pathways.

Materials and Methods
i) Yeast Strains
A yeast *Saccharomyces cerevisiae* strain used in this study was PSY315 (Mat a, leu2, ura3 his3, lys2).
ii) Yeast Transformation and Media
The LiCl method (Ito et al., *J. Bacteriol.* 153: 167 (1983)) was used for yeast transformation. Following media were used for yeast culture, YPD (1% yeast extract, 2% tryptone, 2% glucose), YPG (1% yeast extract, 2% tryptone, 2% galactose), SD (0.067% yeast nitrogen base w/o amino acids, 2% glucose), and SG (0.067% yeast nitrogen base w/o amino acids, 2% galactose).
iii) Plasmids
The vector plasmids pTS210 and pTS249 carry URA3 and LEU2, respectively, and both carry CEN4, GAL1 promoter and ACT1 terminator. The plasmid pKNA1 harbors LEU2, CEN4, ACT1 promoter and ACT 1 terminator.
Two types of plasmids for expression of Xenopus bFGF (basic fibroblast growth factor) in yeast were constructed: One plasmid is constructed by cloning bFGF gene into pTS210 (pTS-FGF) and a second plasmid is identical to the first except that a signal sequence of *S. cerevisiae* invertase (Carlson et al., *Mol. Cell. Biol.* 3: 439 (1983)) was inserted at the initiation codon of the bFGF gene (pTS-ssFGF). For FGF receptor expression, the Xenopus FGF receptor-1 gene (Musci et al., *Proc. Natl. Acad. Sci. USA* 87: 8365 (1990)) was cloned into pTS249 and pKNA1 (pTS-FGFR and pKN-FGFR, respectively).
iv) Antibody
Anti-phosphotyrosine antibody 4G10 is purchased from Upstate Biotechnology Incorporated.

v) Colony Western Blotting

Yeast transformants were plated on SD plates and incubated at 30° C. for two days. Colonies were transferred onto two nitrocellulose membranes (Millipore HATF 082). These membranes were placed colony-side up on SD and SG plates, and incubated overnight at 30° C. The membranes were placed on Whatman 3MM filter paper pre-soaked with lysis buffer (0.1% SDS, 0.2 M NaOH, 35 mM DTT), and incubated at room temperature for 30 min. Colonies on the membranes were rinsed off with water, then the membranes were incubated in TBS-T(20 mM Tris-HCl pH 8.0, 150 mM NaCl, 0.05% Tween-20)–2% BSA (sigma) for blocking on a shaker for one hour, then incubated in 1:1,000-diluted anti-phosphotyrosine antibody (in TBS-T with 2% BSA) for one hour, and subsequently washed three times in TBS-T. The blots were then incubated in 1:10,000-diluted HRP (horse radish peroxidase)—conjugated goat anti-mouse Ig antibody (Bio-Rad) for one hour, and washed three times. Detection was done with chemiluminescence reagents (Amersham, ECL).

vi) cDNA Library

The vector plasmid of the cDNA library is λyes (Elledge et al., *Proc. Natl. Acad. Sci. USA* 88: 1731 (1991)), which carries URA3, CEN4, ARS1, GAL1 promoter and HIS3 terminator. Two sources of cDNA were used for library construction. One was made from Xenopus XTC cells, The other was made from Xenopus unfertilized eggs and 10 hour embryos.

vii) $Ca^{2+}$ Release Assay

The procedure for the $Ca^{2+}$ release assay described in Amaya et al. (*Cell* 66: 257 (1991)) was followed. Briefly, oocytes injected with certain mRNAs transcribed in vitro were incubated for two days, then incubated with $^{45}Ca^{2+}$ for three hours. These oocytes were washed in $^{45}Ca^{2+}$-free medium, incubated in media for 10 minutes, followed by scintillation counting of the released radioactivity.

viii) Partial Purification of EG2 Protein

Yeast cells expressing the EG2 gene under control of GAL promoter were cultured in 1 L of YPG for eight hours (about $2 \times 10^{10}$ cells). Cells were collected and disrupted with glass beads in 20 ml of buffer A (20 mM Tris-HCl (pH 8.0), 1 mM EDTA, 1 mM PMSF), containing 150 mM NaCl. Cell debris were removed by low speed centrifugation (3,000×g for 5 minutes). The supernatant was centrifuged at 80,000×g for 20 minutes. The pellet was suspended in 5 ml of buffer A containing 1.2 M NaCl, then centrifuged with the same condition. The resulting pellet was suspended in 2 ml of buffer A containing 1% Triton X-100, and centrifuged with the same condition again. The supernatant was diluted 20 fold in modified Barth's saline (Gurdon, *Meth. Cell Biol.* 16: 125 (1977)) containing 0.5 mg/ml BSA.

Results and Discussion

To test whether co-expression of a receptor-tyrosine kinase and its ligand leads to the activation of the kinase in yeast cells, *Xenopus laevis* FGF receptor and bFGF were used as a model system. These genes were co-expressed in yeast cells under control of GAL1 promoter by co-transforming pTS-FGFR and pTS-FGF. In addition, bFGF fused with the SUC2 signal sequence (pTS-ssFGF) was also co-expressed with the FGF receptor gene because it is known that the bFGF gene does not have a signal sequence.

To determine whether the tyrosine kinase is activated in these strains, whole cell extracts were analyzed by immunoblotting with anti-phosphotyrosine antibody. The following results were obtained: (1) Expression of either bFGF or ssFGF alone had no effect on the level of tyrosine phosphorylation. (2) Expression of the FGF receptor plasmid led to a substantial increase in tyrosine phosphorylation of several endogenous proteins. (3) Co-expression of FGF receptor and ssFGF dramatically increased tyrosine phosphorylation to a level that was several times higher than the phosphorylation level observed after expression of the FGF receptor alone. (4) Co-expression of the FGF receptor and bFGF without a signal sequence did not lead to any increase in phosphorylation above that obtained after expression of the FGF receptor alone, although the same levels of the FGF proteins in the strains expressing the bFGF gene with and without the signal sequence are detected by immunoblotting with anti-FGF antibody. FGF could not be detected in culture supernatants, suggesting that the interaction was intracellular or periplasmic.

These findings demonstrate that it is possible to functionally co-express the FGF receptor and bFGF in yeast in such a way that they can interact productively in an autocrine manner and thereby lead to an increase in the FGF-receptor mediated phosphorylation of endogenous yeast proteins. bFGF with a signal sequence appears to interact with the extracellular domain of the FGF receptor on the cell surface or in internal membrane compartments, while bFGF without a signal sequence localizes in the cytoplasm and cannot interact with the receptor.

For screening of a large number of yeast transformants, a colony Western blotting method (Lyons and Nelson, *Proc. Natl. Acad. Sci. USA* 81: 7426 (1984)) was developed. Yeast transformants expressing bFGF (with or without the signal sequence) and/or FGF receptor were plated on a glucose plate. Colonies were transferred to a filter and the filter was then placed on a galactose plate to induce bFGF expression. After overnight incubation, cells on the filter were lysed and the level of tyrosine phosphorylated proteins in each colony was determined by probing with anti-phosphotyrosine antibodies. The results of this experiment were essentially the same as those described above. That is, expression of the FGF receptor led to an increase in the level of tyrosine phosphorylation that was substantially augmented when bFGF containing a signal sequence was co-expressed, but not when bFGF lacking a signal sequence was co-expressed. These results indicate that the colony Western blotting method is sensitive and can be used to rapidly and easily screen thousands of different yeast colonies.

Several promoters have been tested for the expression of the FGF receptor gene in order to optimize the detection of its activation by colony Western blotting. They included the GAL1, ACT1 (actin; Gallwitz et al., *Nucl. Acids Res.* 9: 6339 (1981)), GPD1 (glyceraldehyde-3-phosphate dehydrogenase; Bitter and Egan, *Gene* 32: 263 (1984)) and TUB1 (α-tubulin; Schatz et al., *Mol. Cell. Biol.* 6: 3711 (1986)) promoters. Among them, the ACT1 promoter was determined to be most suitable. FGF receptor gene expression driven by GAL1 promoter proved very high, leading to high levels of tyrosine phosphorylation even in the absence of FGF, while the TUB1 promoter was extremely weak, such that FGF receptor activation by FGF could not be detected. Under the control of the GPD1 promoter, expression of the FGF receptor gene was repressed by galactose-containing media. On the other hand, the ACT1 promoter gave similar levels of FGF receptor gene expression in galactose- and in glucose-containing media, and levels of tyrosine phosphorylation were low in the absence of FGF, but significantly increased by expression of ssFGF. For these reasons, the ACT1 promoter was used for the cDNA screening experiment described below.

The above results encouraged further attempts to use this method to identify novel ligands for tyrosine kinase receptors. As a first step, the method was used to identify new ligands for the FGF receptor. The purpose of this experiment is two-fold: first, to determine whether this system can be used to identify genuine FGF genes, and second, to isolate previously unidentified activators of the FGF receptor.

Figure 1B:
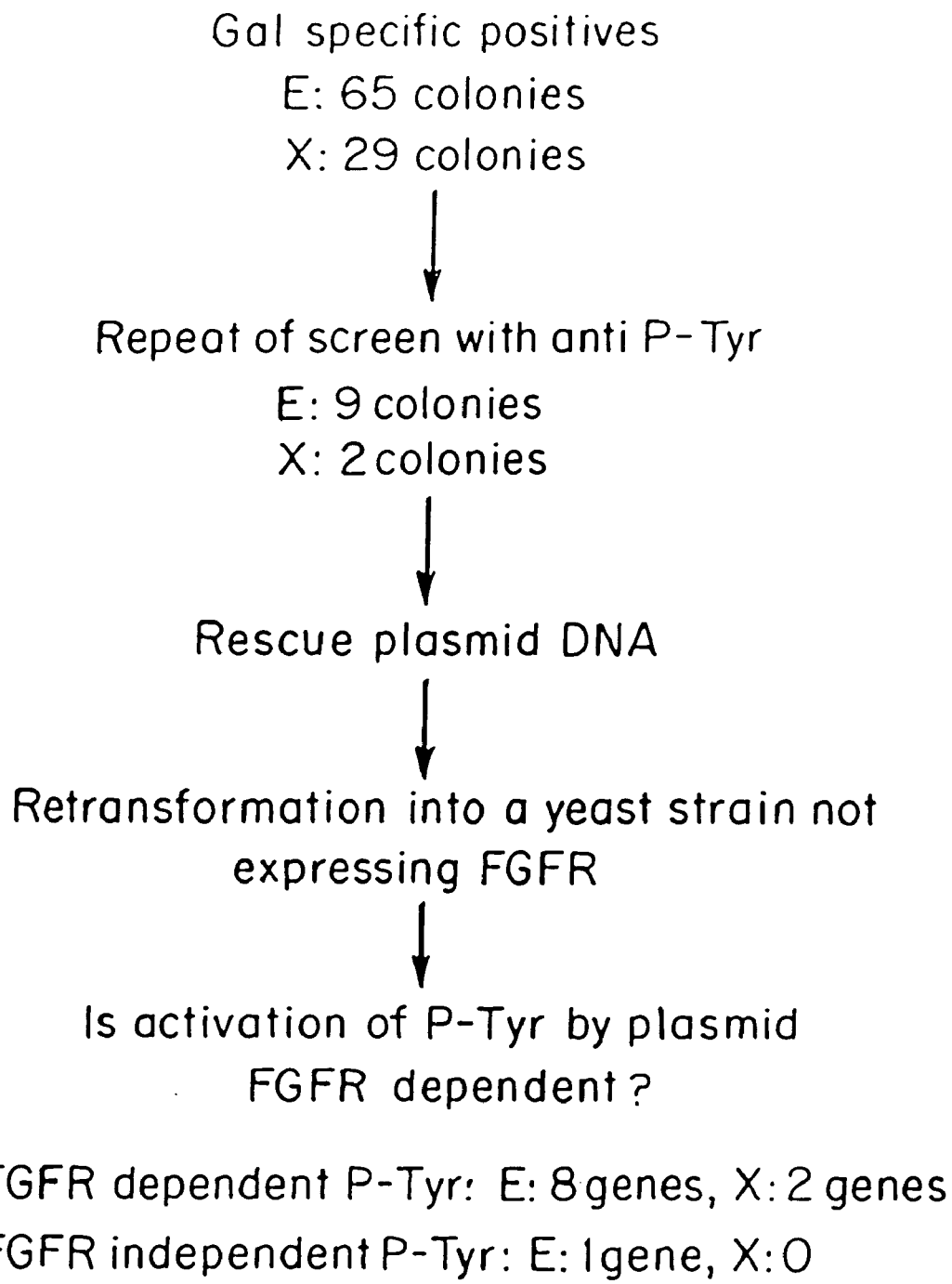

The procedure followed is outlined diagramatically in FIG. 1. Yeast cells expressing the FGF receptor were transformed with a cDNA library expected to contain FGF gene family members. Since bFGF (Kimelman et al., *Science* 242: 1053 (1988)), embryonic FGF (Isaacs et al., *Development* 114: 711 (1992)) and int-2/FGF3 (Tannahill, et al., *Development* 115: 695 (1992)) are known to be expressed in xenopus embryos, we used a cDNA library made from mRNA isolated from Xenopus eggs and embryos (egg library). A library made from XTC cells was also used (XTC library).

150,000 and 25,000 transformants were obtained from the egg and XTC libraries, respectively. In the first screening by colony Western blotting with an anti-phosphotyrosine antibody, 65 and 29 candidates were identified, and by the second screening, nine and two transformants were found to be positive (egg and XTC library, respectively). Plasmid DNA in each transformant was rescued, and re-transformed into yeast strains with and without the FGF receptor gene in order to test whether the positive signal is dependent on expression of the FGF receptor gene. Only one plasmid rescued from one of the egg-library transformants was found to be positive even in the absence of the receptor gene expression. The other genes increased tyrosine phosphorylation only when the FGF receptor gene was co-expressed.

The DNA sequence of the genes present on these plasmids was determined (Table 1). Two genes encoded peptide factors with putative signal peptide sequences. One gene, designated XT1, encodes a protein with some homology to bovine angiogenin and Chinese hamster pancreatic ribonuclease A (about 30% identity; (Maes et al., *FEBS Letter* 241: 41 (1988); Haugg and Schein, *Nucl. Acids Res.* 20: 612 (1992)). The other, EG2, is homologous to cripto, which is an EGF family member, identified in both mouse and human (about 30% identity; Ciccodicola et al., *EMBO J.* 8: 1897 (1989); Dono et al., *Development* 118: 1157 (1993)). Angiogenin, like FGF, is an angiogenesis-promoting factor. Cripto is suggested to have a role in mesoderm by virtue of its embryonic localized induction. Receptors for angiogenin and cripto have not yet been identified. Taking these facts into account, XT1 and EG2 gene products could be novel ligands of the FGF receptor.

The XT2 encodes a putative protease homologous to cathepsin L (58% identity with human cathepsin L; Joseph et al., *J. Clin. Invest.* 81: 1621 (1988); Gal and Gottesman, *Biochem. J.* 253: 303 (1988)). This protease might cleave the FGF receptor in yeast cells, and the cleaved fragment might have an elevated tyrosine kinase activity. EG1 was previously identified in *Xenopus laevis* as a heterogeneous ribonucleoprotein (Kay et al., *Proc. Natl. Acad. Sci. USA* 87: 1367 (1990)). EG3 has an RNA recognition motif found in many RNA binding proteins (Kim and Baker, *Mol. Cell. Biol.* 13: 174 (1993)). These RNA binding proteins might increase synthesis of FGF receptor protein by increasing the efficiency of transcription or translation. Elevated expression induces autophosphorylation.

EG4 encodes a novel 96 kDa protein. Recently, a gene similar to EG4 was found in C. elegans (39% identity), but its function is unknown (Wilson et al., *Nature* 368: 32 (1994)). The plasmid which was positive even in the absence of the FGF receptor gene harbored a gene encoding a putative tyrosine kinase homologous to mouse cytoplasmic tyrosine kinase FER (Hao et al., *Mol. Cell. Biol.* 9: 1587 (1989)).

XT1 and EG2, which have been identified as activators of the FGF receptor in yeast, were tested to determine whether they could also activate the FGF receptor expressed in higher eukaryotic cells. Since it is known that the activation of FGF receptor in Xenopus oocytes is linked to a rapid $Ca^{2+}$ release from internal stores (Johnson et al., *Mol. Cell. Biol.* 10: 4728 (1990)), $Ca^{2+}$ release assays were performed with Xenopus oocytes expressing FGF receptor.

As for EG2, the EG2 protein was partially purified tagged with a flag epitope expressed in yeast. The oocytes expressing FGF receptor were labeled with $^{45}Ca^{2+}$ treated with EG2, followed by $Ca^{2+}$ release assay. It was found that Ca release was stimulated by treatment of partially purified EG2 protein.

As for XT1, this protein has not been expressed efficiently enough to purify the protein, so instead, XT1 mRNA was co-injected with FGF receptor mRNA into oocytes. If XT1 protein activates the FGF receptor in oocytes, it is expected that the FGF receptor would be constitutively activated by the continuous synthesis of XT1 protein, and that the basal level of $Ca^{2+}$ efflux in the co-injected oocyte would be higher than in oocytes injected FGF receptor mRNA alone. $Ca^{2+}$ efflux of labeled oocytes was measured, and it was found that co-injection of XT1 and FGF receptor mRNAs increased $Ca^{2+}$ release two-fold more than the injection of FGF receptor message alone. Co-injection of bFGF and FGF receptor mRNA increased $Ca^{2+}$ release three-fold. XT1 or bFGF mRNA alone did not increase $Ca^{2+}$ release.

These results demonstrate that XT1 and EG2 can activate FGF receptor expressed in Xenopus oocytes, and that these protein synthesized in vivo can work as activators of FGF receptor. In order to demonstrate that these proteins are real ligands for FGF receptor, it will be necessary to show that these proteins bind directly to an extracellular domain of the FGF receptor.

TABLE 1

Genes Which Increase Protein-Tyrosine Phosphorylation in Yeast Cells Expressing FGF Receptor.

| gene | FGF receptor dependency | gene product | frequency of isolation |
|---|---|---|---|
| 1) secreted proteins | | | |
| XT1 | + | homologous to angiogenin and RNaseA | 1 |
| EG2 | + | cripto (EGF-like growth factor) | 4 |
| XT2 | + | 58% identical to human cathepsin L | 1 |
| 2) RNA binding proteins | | | |
| EG1 | + | heterogeneous ribonucleoprotein | 2 |
| EG3 | + | RNA binding protein | 1 |
| 3) a novel protein | | | |
| EG4 | + | novel 96 kd protein | 1 |
| 4) FGF-receptor independent | | | |
| EG5 | – | cytoplasmic tryosine kinase TER | 1 |

We claim:

1. A method for identifying a ligand for a receptor tyrosine kinase, comprising:
    a) providing a cDNA expression library from an organism of interest;
    b) providing a population of yeast cells that constitutively express a copy of a gene encoding a heterologous receptor tyrosine kinase;

c) transforming the population of yeast cells of step b) with the cDNA expression library of step a); and d) detecting intracellular enzymatic protein kinase activity in clonally-derived yeast cells as an indication of the presence of DNA encoding a ligand for the heterologous receptor tyrosine kinase in the clonally-derived yeast cells.

2. A method of claim 1 wherein the gene encoding the heterologous receptor tyrosine kinase is carried on a CEN-based plasmid.

3. A method of claim 1 wherein the gene encoding the heterologous receptor tyrosine kinase is inserted into a yeast chromosome.

4. A method of claim 1 wherein the expression of the cDNA insert in the cDNA library is under the control of an inducible promoter.

5. A method of claim 1 wherein the heterologous receptor tyrosine kinase is derived from a mammalian source.

6. A method of claim 1 wherein the heterologous receptor tyrosine kinase is a cytokine receptor.

7. A method of claim 1 wherein the heterologous receptor tyrosine kinase has the ability to activate a heterologous cytoplasmic tyrosine kinase activity in response to ligand binding.

8. A method of claim 1 wherein the cDNA expression library is derived from a mammalian source.

9. A method for identifying a ligand for a transmembrane receptor having a single transmembrane domain, an extracellular domain and an intracellular domain, comprising:

a) providing a cDNA expression library from an organism of interest;

b) providing a population of yeast cells that constitutively express a copy of a gene encoding a chimeric transmembrane receptor, the chimeric transmembrane receptor comprising the extracellular domain of a transmembrane receptor, the extracellular domain originating in a receptor having only one extracellular, one transmembrane and one cytoplasmic domain, and an intracellular domain from a receptor tyrosine kinase;

c) transforming the population of yeast cells of step b) with the cDNA expression library of step a); and d) detecting intracellular enzymatic protein kinase activity in clonally-derived yeast cells as an indication of the presence of DNA encoding a ligand for the chimeric transmembrane receptor in the clonally-derived yeast cells.

10. A method of claim 9 wherein the chimeric transmembrane receptor comprises an intracellular domain of a first receptor tyrosine kinase fused to the extracellular domain of a second receptor tyrosine kinase.

11. A method of claim 10 wherein the intracellular domain of the chimeric transmembrane receptor exhibits cytoplasmic tyrosine kinase activity in response to ligand binding.

12. A method of claim 9 wherein the chimeric transmembrane receptor comprises an intracellular domain of a tyrosine kinase fused to the extracellular domain of a tyrosine phosphatase receptor.

13. A method of claim 12 wherein the intracellular domain of the chimeric transmembrane receptor exhibits cytoplasmic tyrosine kinase activity in response to ligand binding.

14. The method of claim 9 wherein the extracellular domain corresponds to the extracellular domain of a cytokine receptor.

* * * * *